(12) United States Patent
Friedmann et al.

(10) Patent No.: US 12,280,248 B2
(45) Date of Patent: **\*Apr. 22, 2025**

(54) SINGLE USE SAFETY NEEDLE GUARD

(71) Applicant: FGC Holdings Limited, North York (CA)

(72) Inventors: Peter Friedmann, North York (CA); Jonathan Liberty, Etobicoke (CA)

(73) Assignee: FGC Holdings Limited

( * ) Notice: Subject to any disclaimer, the term of this patent is extended or adjusted under 35 U.S.C. 154(b) by 0 days.

This patent is subject to a terminal disclaimer.

(21) Appl. No.: 18/504,574

(22) Filed: Nov. 8, 2023

(65) Prior Publication Data

US 2024/0082508 A1 Mar. 14, 2024

Related U.S. Application Data

(63) Continuation of application No. 17/665,280, filed on Feb. 4, 2022, now Pat. No. 11,833,337, which is a continuation of application No. 16/665,662, filed on Oct. 28, 2019, now Pat. No. 11,266,792.

(51) Int. Cl.
*A61M 5/32* (2006.01)

(52) U.S. Cl.
CPC ........ *A61M 5/3275* (2013.01); *A61M 5/3202* (2013.01); *A61M 5/3271* (2013.01); *A61M 2005/3247* (2013.01)

(58) Field of Classification Search
CPC .............. A61M 5/3275; A61M 5/3202; A61M 5/3271; A61M 2005/3247
See application file for complete search history.

(56) References Cited

U.S. PATENT DOCUMENTS

| | | | |
|---|---|---|---|
| 3,330,004 | A | 7/1967 | Cloyd et al. |
| 4,735,618 | A | 4/1988 | Hagen |
| 4,935,013 | A | 6/1990 | Haber et al. |
| 5,078,697 | A | 1/1992 | Rammler |
| 5,348,544 | A | 9/1994 | Sweeney et al. |

(Continued)

FOREIGN PATENT DOCUMENTS

| | | |
|---|---|---|
| CN | 1355716 A | 6/2002 |
| CN | 1449846 A | 10/2003 |

(Continued)

OTHER PUBLICATIONS

PCT International Search Report and Written Opinion, International Application No. PCT/IB2020/000906, dated Mar. 22, 2021, 8 pages.

(Continued)

*Primary Examiner* — Theodore J Stigell
(74) *Attorney, Agent, or Firm* — Barley Snyder

(57) ABSTRACT

A Hypodermic Needle Safety Guard intended for sharps prevention and safer hypodermic needle use during all stages of an injection process. The Safety Guard may include two symmetrically positioned multi-featured arms that include spring tension, multiple hinges and needle locks. These arms may connect a proximal Luer body and a distal alignment tip thereby enabling the guard to open, close and lock on a needle when manual pressure is applied. The Guard position during hypodermic needle use tends to prevent sharps injury by adjusting the exposure of the Needle tip.

8 Claims, 21 Drawing Sheets

(56) References Cited

U.S. PATENT DOCUMENTS

| | | | |
|---|---|---|---|
| 5,509,907 | A | 4/1996 | Bevilacqua |
| 5,578,011 | A | 11/1996 | Shaw |
| 5,584,818 | A | 12/1996 | Morrison |
| 5,632,733 | A | 5/1997 | Shaw |
| 5,951,525 | A * | 9/1999 | Thorne ............ A61M 25/0637 604/162 |
| 6,090,077 | A | 7/2000 | Shaw |
| 6,171,284 | B1 | 1/2001 | Kao et al. |
| 6,409,706 | B1 | 6/2002 | Loy |
| 6,461,328 | B2 | 10/2002 | Wang et al. |
| 6,972,002 | B2 | 6/2005 | Thorne |
| 6,986,759 | B1 | 1/2006 | Jeremijevic |
| 7,300,423 | B2 | 11/2007 | Cocker et al. |
| 7,461,871 | B2 | 12/2008 | Vauchel |
| 7,465,294 | B1 | 12/2008 | Vladimirsky |
| 7,922,698 | B2 | 4/2011 | Riesenberger et al. |
| 7,972,313 | B2 | 7/2011 | Woehr et al. |
| 8,016,772 | B2 | 9/2011 | Heske et al. |
| 8,034,060 | B2 | 10/2011 | Keren et al. |
| 8,048,036 | B2 | 11/2011 | Woehr et al. |
| 8,052,614 | B2 | 11/2011 | Heske et al. |
| 8,109,885 | B2 | 2/2012 | Heske et al. |
| 8,172,773 | B2 | 5/2012 | Heske et al. |
| 8,211,070 | B2 | 7/2012 | Woehr et al. |
| 8,277,409 | B2 | 10/2012 | Summerville et al. |
| 8,303,621 | B2 | 11/2012 | Miyamoto et al. |
| 8,328,766 | B2 | 12/2012 | Liversidge |
| 8,382,721 | B2 | 2/2013 | Woehr et al. |
| 8,449,505 | B2 | 5/2013 | Lin Lee |
| 8,449,559 | B2 | 5/2013 | Keren et al. |
| 8,460,241 | B2 | 6/2013 | Grimard |
| 8,460,249 | B2 | 6/2013 | Woehr |
| 8,486,016 | B2 | 7/2013 | Kanbar et al. |
| 8,486,024 | B2 | 7/2013 | Steube |
| 8,496,619 | B2 | 7/2013 | Kramer et al. |
| 8,500,699 | B2 | 8/2013 | Millerd |
| 8,529,515 | B2 | 9/2013 | Woehr et al. |
| 8,529,522 | B2 | 9/2013 | Cohen |
| 8,535,257 | B1 | 9/2013 | Zelten et al. |
| 8,535,271 | B2 | 9/2013 | Fuchs et al. |
| 8,540,728 | B2 | 9/2013 | Woehr et al. |
| 8,545,454 | B2 | 10/2013 | Kuracina et al. |
| 8,551,047 | B2 | 10/2013 | Burns et al. |
| 8,556,853 | B2 | 10/2013 | Vaillancourt et al. |
| 8,561,434 | B2 | 10/2013 | Busi |
| 8,562,564 | B2 | 10/2013 | Lesch, Jr. |
| 8,568,372 | B2 | 10/2013 | Woehr et al. |
| 8,574,188 | B2 | 11/2013 | Potter et al. |
| 8,585,650 | B2 | 11/2013 | Carrez et al. |
| 8,590,193 | B2 | 11/2013 | Licha |
| 8,591,465 | B2 | 11/2013 | Hommann |
| 8,591,474 | B2 | 11/2013 | Gratwohl et al. |
| 8,591,475 | B2 | 11/2013 | Grady |
| 8,608,692 | B2 | 12/2013 | Agrawal |
| 8,608,693 | B2 | 12/2013 | Westbye |
| 8,613,728 | B2 | 12/2013 | Amisar et al. |
| 8,617,122 | B2 | 12/2013 | Judd et al. |
| 8,628,498 | B2 | 1/2014 | Safabash et al. |
| 8,628,501 | B2 | 1/2014 | Hadden |
| 8,636,703 | B2 | 1/2014 | Foshee et al. |
| 8,647,301 | B2 | 2/2014 | Bialecki et al. |
| 8,647,306 | B2 | 2/2014 | Schwirtz et al. |
| 8,647,307 | B2 | 2/2014 | Gratwohl et al. |
| 8,647,313 | B2 | 2/2014 | Woehr et al. |
| 10,441,727 | B2 | 10/2019 | Shimer et al. |
| 11,266,792 | B2 * | 3/2022 | Friedmann .......... A61M 5/3275 |
| 11,833,337 | B2 * | 12/2023 | Friedmann .......... A61M 5/3202 |
| 2003/0149404 | A1 | 8/2003 | Lehmann |
| 2003/0181871 | A1 | 9/2003 | Wilkinson et al. |
| 2003/0181872 | A1 | 9/2003 | Newby |
| 2004/0162532 | A1 | 8/2004 | Cocker et al. |
| 2007/0100296 | A1 | 5/2007 | Hwang |
| 2009/0171285 | A1 | 7/2009 | Wang |
| 2010/0298739 | A1 | 11/2010 | Steube et al. |
| 2012/0184910 | A1 | 7/2012 | Woehr |
| 2012/0197201 | A1 | 8/2012 | Tanabe et al. |
| 2012/0220957 | A1 | 8/2012 | Kuracina et al. |
| 2013/0030376 | A1 | 1/2013 | Doyle et al. |
| 2013/0261559 | A1 | 10/2013 | Webickas |
| 2015/0359967 | A1 | 12/2015 | Steel et al. |

FOREIGN PATENT DOCUMENTS

| | | |
|---|---|---|
| CN | 1816675 A | 8/2006 |
| CN | 203848211 U | 9/2014 |
| CN | 108778369 A | 11/2018 |
| FR | 2734727 A1 | 5/1995 |
| GB | 2560508 A | 9/2018 |
| JP | 2004033734 A | 2/2004 |
| WO | 0016832 A | 3/2000 |

OTHER PUBLICATIONS

Extended European Search Report dated Oct. 9, 2023, corresponding to Application No. 0882504.2-1122/4051348 PCT/IB2020000906, 10 pages.
First Chinese Office Action dated Nov. 13, 2023 with English translation, corresponding to Application No. 202080089924.7, 23 pages.
Japanese Office Action dated Aug. 30, 2024 with English translation, corresponding to Application No. 2022-525594, 26 pages.
Indian Office Action dated Oct. 4, 2024 with English translation, corresponding to Application No. 202227025985, 6 pages.

* cited by examiner

SINGLE USE SAFETY NEEDLE GUARD

CROSS-REFERENCE TO RELATED APPLICATIONS

The application is a continuation of U.S. application Ser. No. 17/665,280 filed on Feb. 4, 2022 which is a continuation of Ser. No. 16/665,662, filed on Oct. 28, 2019, now U.S. Pat. No. 11,266,792.

BACKGROUND

There are multiple types of safety Guards that are integrated with or attach to hypodermic Needles of syringes in the market today. Guards are primarily used in the transport and storage of hypodermic needles. Guards tend to not remain in use during the filling and use of the syringe and tends to require placement of a user's hands near the Needle Tip to remove and place the Guard onto a Needle and increasing the risk of accidental injury or contamination. There exists a need for a Needle Guard that stays in place on a syringe and needle, and that is safer for users.

SUMMARY

In an embodiment of the invention, there is a Guard that remains on or near the Needle during all phases of the use of a hypodermic Needle. In the embodiment, the Guard changes shape during its use or operation, such as when the Needle is stored, filled, transported, used, or prevented from use.

In an embodiment, a single use Needle safety Guard covers a hypodermic Needle that prevents the Needle from causing sharps injury such as during transport and storage, and still allows the Needle to be used without manual detachment of the Guard from the Needle or syringe. The Guard tends to be useful from storage to filling a syringe with fluid, to transporting it around and the administration of the fluid, to potentially also before "locked" for disposal. Such a Guard can function to prevent sharps injuries during the use of a hypodermic Needle before its disposal, and alternate embodiments can also function alternatively or additionally to prevent secondary use of the Needle.

In an embodiment, there is a hypodermic or injectable Needle Guard, configured to reduce the possibility of sharps injuries and increasing overall use safety. The Guard of the embodiment can be permanently affixed to a Needle body and configured to form during the use of the Needle to provide greater use safety. The Guard can be configured to change form from a first form for storage/travel, to a second form for filling/administration and to a third form for resisting further use. In the embodiment, form can be changed by means of integral or feature formed hinges, and with positional Needle locks. Such form changes tend to allow a greater degree of flexibility and safety during the use cycle of a Needle because as so configured, the Guard does not have to leave or be detached off the Needle or syringe. A Guard of an embodiment can further provide functional benefits in the administration of the fluid because it stays in place. For example, a Guard face can be configured to expand the pressure footprint on skin surface during use to lessen the feeling associated to an injection. In an embodiment, a single use feature can be achieved by means of a Guard having one-time locking features that, for example, position around the Shaft of a Needle making secondary use only possible with the destruction of the Guard.

In an embodiment, there is a guard apparatus for a hypodermic needle. The guard comprises a needle surround adapted to a needle shaft therethrough, and at least two arms extending from the needle surround, each arm moveable from a first position to a second position, and where in the first position each arm runs substantially the length of the needle shaft. When the at least two arms are moved into the second position, the arms bring the needle surround around the needle shaft to allow a portion of the length of the needle shaft therethrough.

Each of the at least two arms may be adapted to reshaping each arm from the first position to the second position. The reshaping of each arm may be provided by two or more hinges on each arm. A first hinge may be proximate to the needle surround, and a second hinge may be positioned further along each arm distal from the first hinge.

An arm may be molded plastic, and each hinge is provided by a thinned section of plastic that is more flexible than other sections of the arms. The thinned section of plastic the arms hinge may be manufactured with forms creating intrinsic varying spring values. The needle surround may be molded plastic. The arms and the needle surround may be molded together.

An arm may have thereon a retention feature adapted to removably engage with the needle shaft when the arm is in the first position, and when the retention feature is removably engaged with the needle shaft, the feature may provide a resistive force against moving the arm from the first position of the arm running substantially along the length of the needle shaft, to the second position. Upon a releasing force overcoming the resistive force is applied, the retention feature may be disengaged from the needle shaft to permit the retention feature to move to the second position. An arm may comprise a second retention feature. The second retention feature may be engageable with the needle when the arm is moved to a third locked position. The second retention feature may provide a locking force greater than the releasing force, to maintain the arm in a locked position whereby the arm runs substantially along the length of the needle shaft. The retention feature may be triangular shaped. The retention feature may be less than 60% of the diameter of the needle shaft. The second retention feature may be triangular shaped. The second retention feature may be 60% or greater than the diameter of the needle shaft.

The first and second retention features may each be grooves molded onto a retention feature arm extending from the arm. The retention feature arm may be molded together with the arm. The second retention feature may be closer to the arm than the first retention feature.

The first retention feature may comprise a first set of grooves, and the second retention feature may comprise a second set of grooves. Each groove of the first set of grooves and each groove of the second set of grooves, respectively, may be molded onto a separate retention feature arm extending from the arm. Each such retention feature arms may be molded together with the arm. Each groove of the second set of grooves may be closer to the arm than each groove of the first set of grooves.

The first retention feature may comprise a triangular-shaped engagement block on a first retention feature arm extending a first distance from the arm. The second retention feature may comprise a triangular-shaped engagement block on a second retention feature arm extending a second distance from the arm. The second distance may be shorter than the first distance.

The guard apparatus may be integrated with a needle body housing of the hypodermic needle connected to the needle shaft. The guard apparatus may be attachable to a needle body housing of the hypodermic needle connected to the needle shaft. The guard apparatus may be attachable to the needle body housing by a Luer lock.

DETAILED DESCRIPTION OF THE EMBODIMENTS

Figure 1:
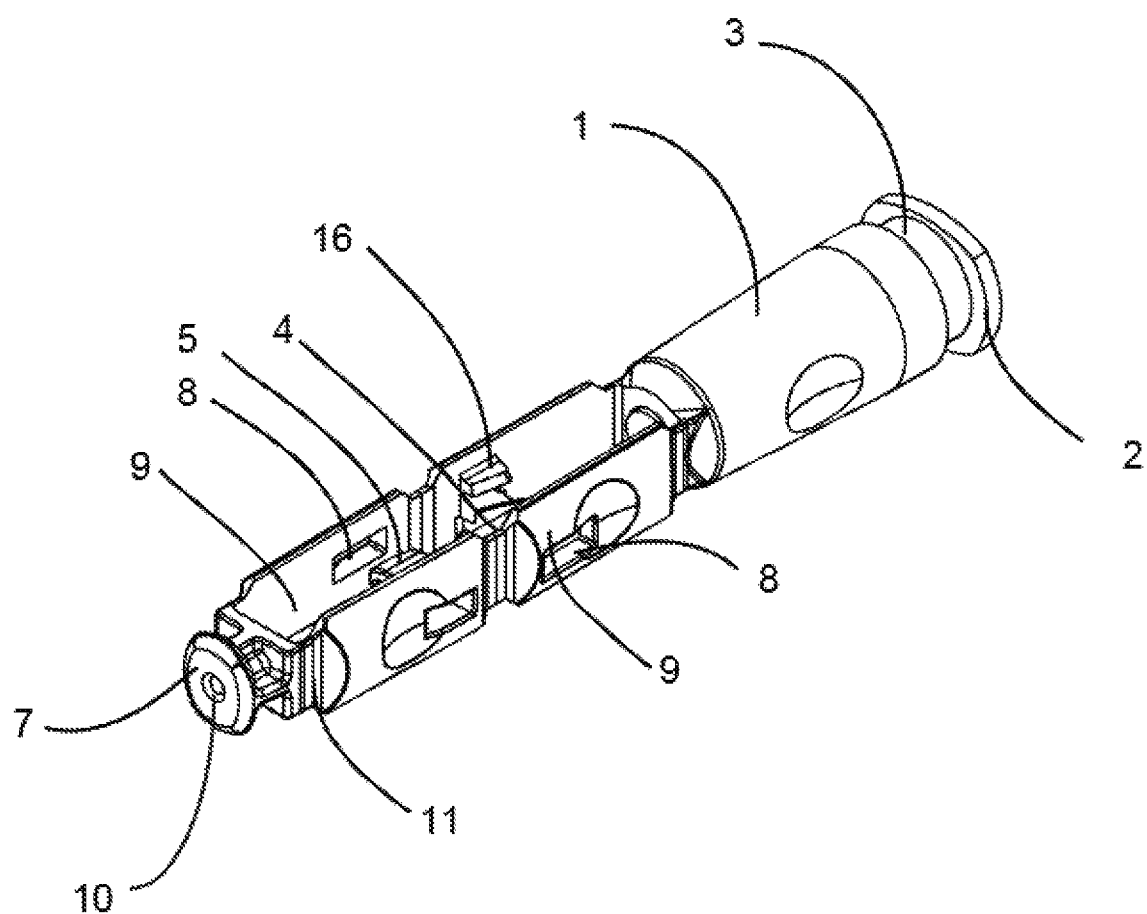
FIG. 1 is an isometric view of a Needle Guard assembled on to a Needle.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures, and components have not been described in detail so as not to obscure the embodiments described herein. Furthermore, this description is not to be considered as limiting the scope of the embodiments described herein in any way, but rather as merely describing the implementation of the various embodiments described herein.

In an embodiment of the invention is an attachable Needle Guard for a hypodermic Needle or an integrated Needle and Guard that protects users from accidental sharps injuries, where once assembled onto the Needle, the Guard is designed to be permanently attached to the needle. In an embodiment, a Guard can be made up of two arms that extend from a central body over two or more sides of a Needle Shaft and extend forward a solid body with a central Needle hole and in front of the Needle Tip. The arms extending forward are capable of flexing and reshaping, such as by means of hinges, which may be integral. In an embodiment, these hinges can be thinned areas of plastics part that allow it to flex and reshape. As configured, when a force is applied to the front of a Guard, portions of the arms on the Guard can flex away from the Needle Shaft by way of the hinges. The direction(s), angle(s) and/or position(s) of flex can be controlled by the initial forming or manufacturer of the Guard. For example, during the molding process the arms may be positioned so that when pressure is applied to the front of the Guard, the arms can flex open in an outward direction to allow the Needle to extend past the face of the Guard (or to withdraw the face of the Guard so that the Needle is exposed). When the force is removed from the front face of the Guard, the arms can be configured so that they return to a partially open form and protect the Needle and its Tip. In an embodiment, the position can be controlled by lock features that extend from the inner surfaces of the arms. These locks can be positional. The lock features position can be configured around the Needle Shaft, such as for temporary and permanent locks. In an embodiment, the temporary locks can engage to prevent sharps injuries during transport or general use, while the permanent locks can engage so that the Needle can be disposed of, such as after use to resist re-use. In an embodiment, the locks can be fully engaged by means of pinching the arms together and towards the Shaft. When the arms are pinched inwards towards the Needle Shaft, the arms change form from capable of opening, such as in a concave shape, to one where they are locked by the locking features and become resistant to opening, such as in a convex shape.

The Locking feature for the needle shaft may be comprised of multiple parts on each arm. In the current embodiment there is a primary and secondary feature. The primary feature provides the initial needle hold position and then a secondary permanent lock. The difference in the position and locking functions are surface features. These features vary in height providing different degrees of interference during assembly. I.e., When the face of the Guard is pressed, the Guard opens, and the Needle extends. The interference required for this change in shape is minimal. When the Guard is pinched for disposal the amount of interference is greater and is intended to not be overcome. Further the shape of the interference during the disposal step can be linear or inclined to allow for constant or increasing force requirements.

The current embodiment incorporates a triangular shaped feature resulting in an increasing force requirement. Secondary to the primary feature is an additional feature above or offset from the first feature. It's positioning creates a lock to the first feature for the needle. If through deformation the Guard is manipulated the Needle is locked in position permanently by the secondary feature. This feature may additionally be shaped to provide constant and increasing force requirements. In addition to the general safety function of the Needle Guard, the Guard can also provide a greater surface area through the face of the guard on the skin when the Needle is inserted into it. This increased surface area can tend to reduce the amount of pain the user feels during the administration of a Needle.

For example, in an embodiment the form of a needle guard can change during its use cycle by means of applied pressure. When the front face of the guard is placed in contact with a body and force is then applied to the needle body, the arms of the Guard will open, and the Needle Tip is then able to extend past the face of the Guard. As the Guard arms open the spring features of the integral hinges are compressed. In such an embodiment, the force applied to the Needle Body so that the Needle Tip extends into the subject body must be greater than the force needed for the spring in the hinge to collapse or open. When the forward moving force is removed or is less than the spring hinge force the Guard Arms begin to return to substantially their initial extended form. Force will not be stored in the Spring Arms if there is no force applied to the face of the Guard.

Referring now to FIG. 1, an exemplary Needle Guard 1 is shown and assembled on a hypodermic Needle 2. As shown, the Guard 1 is sized fit and permanently assembled onto the Needle body 3 of the Needle 2. The Guard may be optionally interference fit on a Hypodermic Needle. The Needle Guard 1 is positioned on the body of the Needle 3 and have arms 9 around Needle Shaft 4. In this embodiment, locking features are provided by way of Shaft locks (or retention feature) 5 positioned around the Needle Shaft 4, which in the embodiment can also hold the Guard 1 in a partially open position. In an embodiment, a partially open, or less open, position can be defined by grooves on tabs extending from the Arms. These grooves allow the Needle to slip in and out of a lock position by means of a two-way feature. The bidirectional feature can be achieved by means of reduced lead-ins and a shallower depth. There is also shown pinch locations 6 on Guard 1 that can be used to apply pressure thereon to close Guard 1 around Needle Shaft 4, when Needle 2 has been used and is ready for disposal. Front face 7 on Guard 1 is additionally shown, along with relief cut-outs 8 in arms 9 that can accommodate Shaft locks 5 to occupy when Guard 1 is in a more open position, such as when the Guard is fully open.

Figure 2:
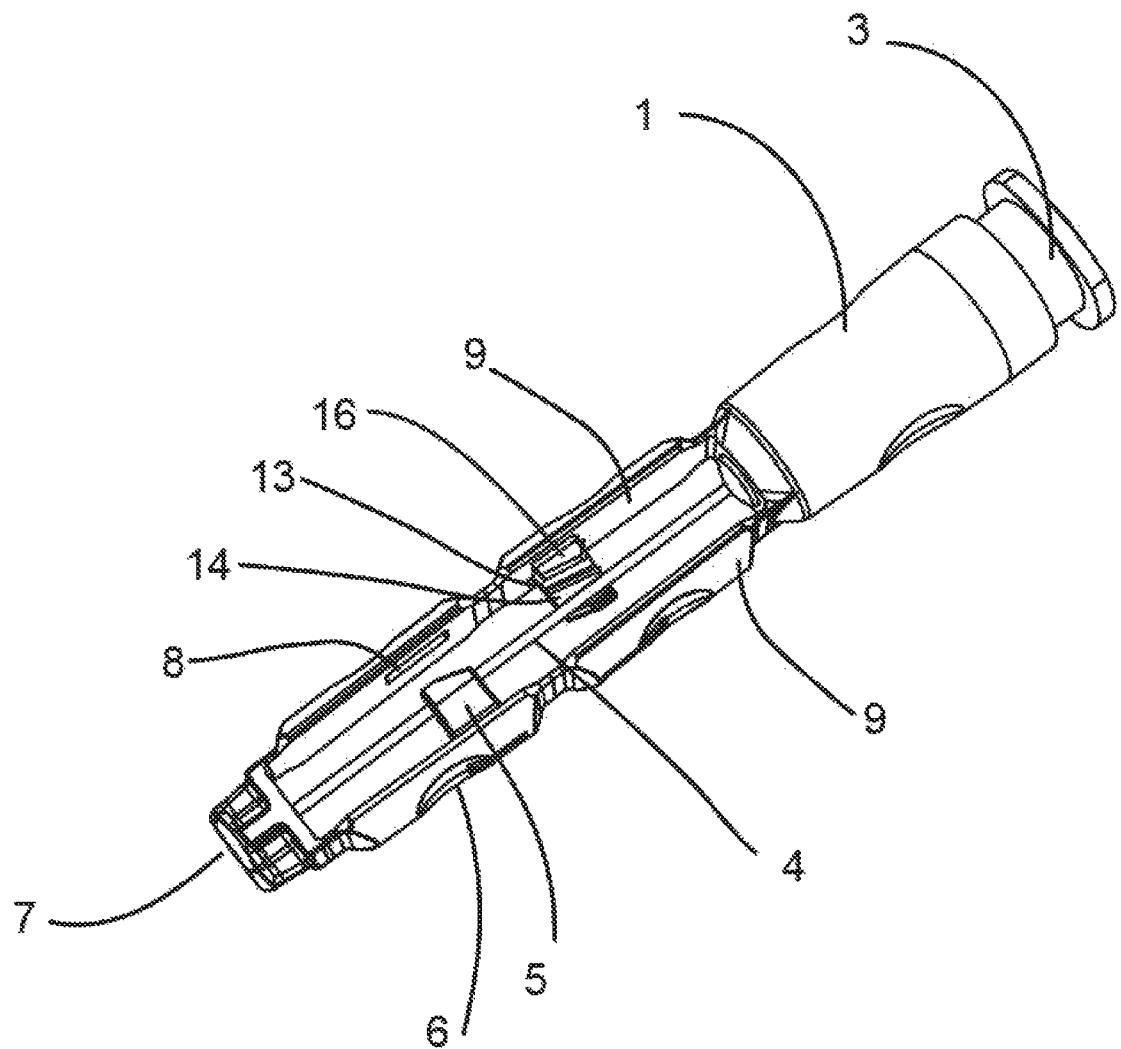
FIG. 2 is another isometric view of the assembled Needle Guard and Needle of FIG. 1.

Referring now to FIG. 2, there is shown an isometric view of Guard 1 with the orientation of the pinch locations 6 shown in top and bottom positions. This view shows Shaft locks 5 and Guard 1, arm 9 and cut-outs 8 from a second viewpoint. Also shown are integral hinges 11 in the arms 9 that in the embodiment allow Guard 1 to flex open and closed during its use in different positions. As shown Guard 1 has front face 7, showing that Needle 2 may pass through hole 10 when Guard 1 opens into a second position.

Figure 3:
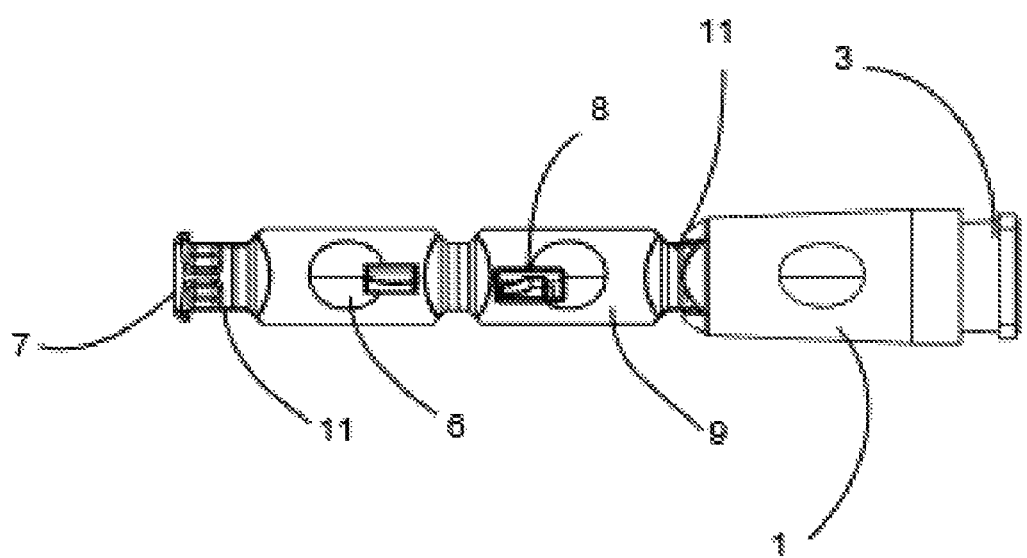
FIG. 3 is a top view of the Needle Guard assembly of FIG. 1.

FIG. 3 is a top view of Guard 1 and Needle 2. It shows the Guard body, arms 9, pinch locations 6, relief cut-outs 8, integral hinges 11 and front face 7. Additionally, it shows the Needle 2, Needle body 3 and Luer lock feature of this embodiment.

Figure 4:
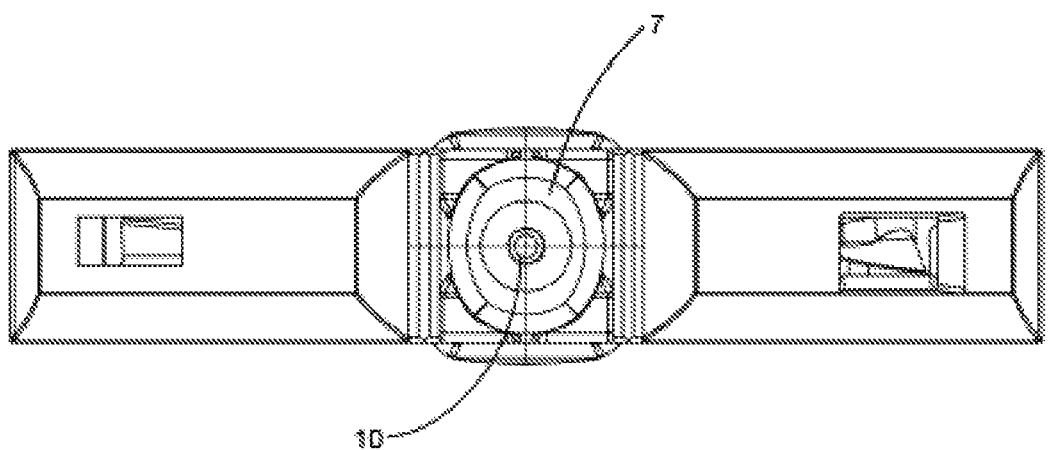
FIG. 4 is a front view of the Needle Guard assembly of FIG. 1.

FIG. 4 shows the front face of the Needle Guard 1 and Needle 2 assembly. This view shows Guard 1's front face 7, pinch locations 6 and body of Needle 1. Needle Shaft 4 can also be seen in the center of the front face 7 and through Needle through hole 10.

Figure 5:
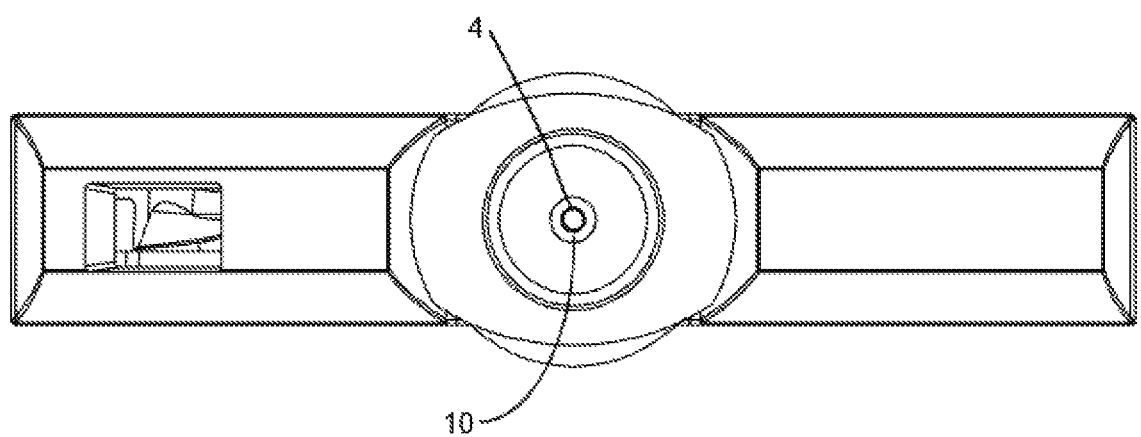
FIG. 5 is a rear view of the Needle Guard assembly if FIG. 1.

FIG. 5 is a rear view of Guard 1 and Needle 2 assembly. There is shown a double D shape of the Needle body 3 and the primary central location of Needle Shaft 4. Also shown are pinch locations 6. in this embodiment, the double-D shape is the feature that mounts in the Luer lock 14 and on a hypodermic Needle body 3.

Figure 6:
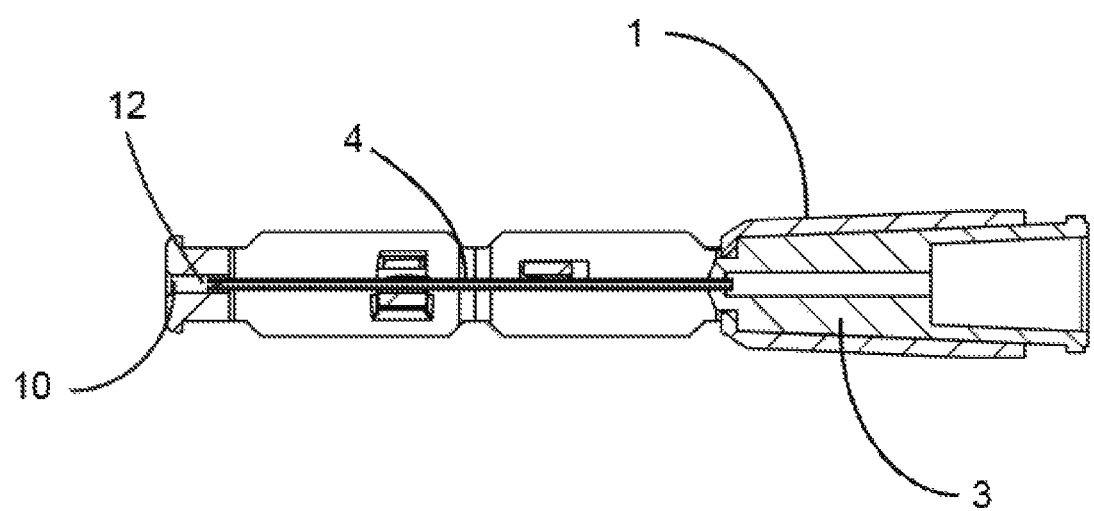
FIG. 6 is a section view of the Needle Guard assembly of FIG. 1.
Figure 7:
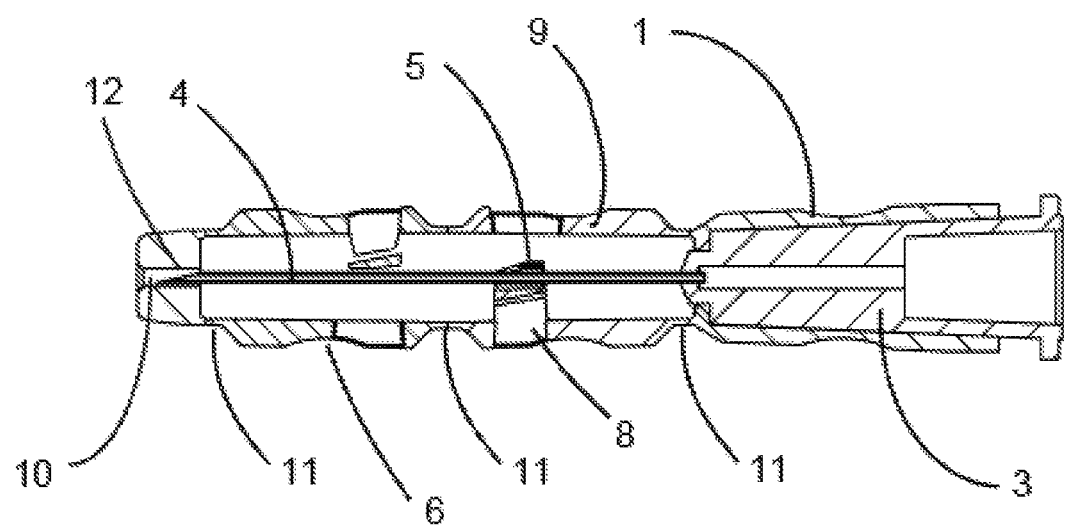
FIG. 7 is another section view of the Needle Guard assembly of FIG. 1.

In FIGS. 6 and 7, there are section views of the assembly in a first, pre-use position of an embodiment. This view shows an assembled assembly of Needle body 3 and Needle Guard 1. Central Needle Shaft 4 and its relationship to Needle Guard 1 can also be seen. The section view also shows Shaft locks 5 configured around Needle Shaft 4, and it shows Needle Tip 12 within the Guard 1 body proximate to front face 7 and positioned to pass through hole 10. This positioning of Needle Tip 12 in the through hole 10, but not extending past the hole, in this position means that the Tip 12 is protected, and users are protected from accidental sharps injury. As configured and shown, the Tip 12 cannot be accessed without locks 5 releasing Needle Shaft 4 and front face 10 moving backwards away from Needle Tip 12 towards the Needle body 3. When locks 5 release from Shaft 4, arms 9 on Guard 1 can flex by means of integral hinges 11.

Figure 8:
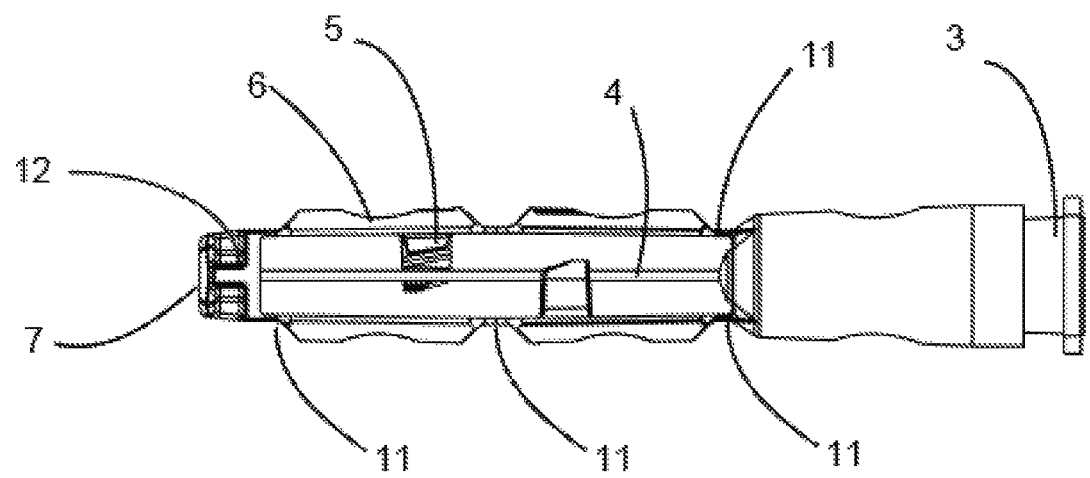
FIG. 8 is a side view of the Needle Guard assembly of FIG. 1, with the Guard in a first position.

FIG. 8 shows a side view of Guard 1 and Needle 2 assembly, showing features of Guard 1. It can be seen body 1, arms 9, integral hinges 11, cut-outs 8 in arms 9, pinch locations 6, Needle Shaft locks 5, Needle Tip 12, Needle Shaft 4, and front face 7. This view also shows an embodiment with integral hinges 11 as thinned sections of arms 9. This thinned section of hinge 11 allows the plastic in an arm 9 to flex in a specific location, which may be adjust along arm 9 as desired.

FIG. 8 further shows arms 9 in their initial molded or formed concave position. This position provides the initial form for arms 9 to move away from. For example, when pressure is applied to the front face 7 of Guard 1, Shaft locks 5 release Shaft 4 and arms 9 of Guard 1 begin to open. In the embodiment shown, opening is the movement of arms 9 so that the angle between them decreases. Their initial form has portions of arms 9 in a substantially flat, or substantially 180 degrees, orientation, with perhaps a small concave relative to Needle Shaft 4 as shown. When arms 9 open, portions of an arm 9 will start to fold as the portions of each arm 9 become substantially parallel.

Figure 9:
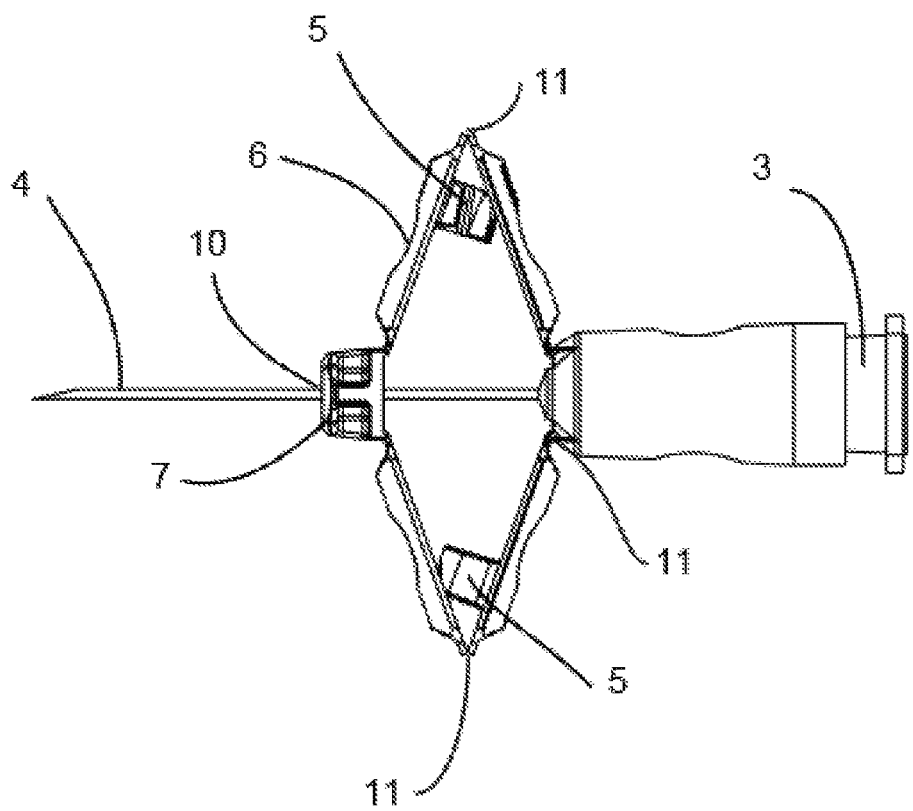
FIG. 9 is another side view of the Needle Guard assembly of FIG. 1, with the Guard in a second position.

FIG. 9 shows a section view of the assembly in an open, or second, position. Here portions of each Guard arms 9 are closer to parallel to one another and the angle between them is closer to zero. As shown, Shaft locks 5 are positioned so that they can occupy complementary cut-outs 8 in arms 9. As shown, Shaft locks 5 in this embodiment has two position locks features. In an embodiment, the lock features can have a first groove in a tab on an arm that has a shallow angled feature on it allows a needle to slide in and out of it multiple times. The tab can also have the ability of flexing with respect to the arm. The lock features can have a second feature which is configured for use as a lock position, which can have steeper angles on it that prevent the needle shaft from sliding in and out once engaged. So, for example, when a needle shaft comes in contact with an angled surface it will be able to move over it. When the shaft comes in contact with a surface perpendicular to it between 45 and 90 degrees the shaft will stop and lock. Such surfaces can be used as locking elements of the embodiment and allow the Guard to lock and unlock on the Needle.

Figure 10:
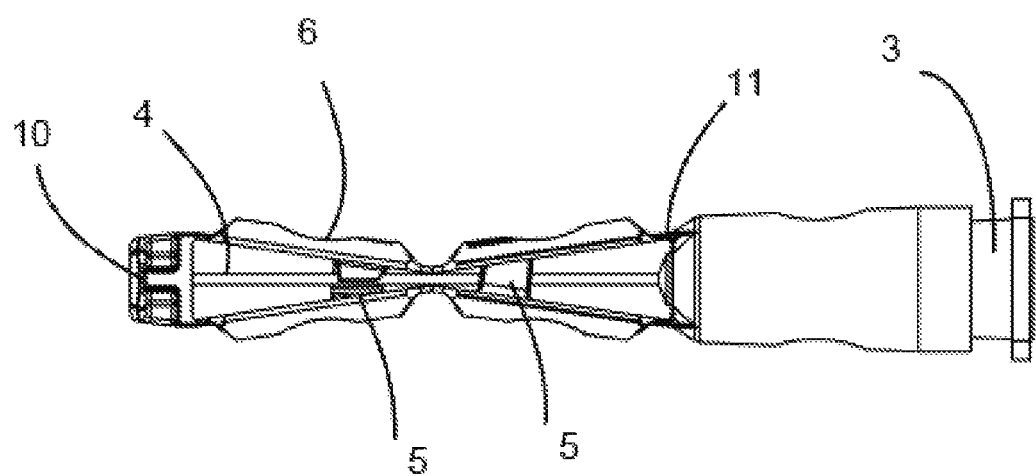
FIG. 10 is another side view of the Needle Guard assembly of FIG. 1, with the Guard in a third position.
Figure 11:
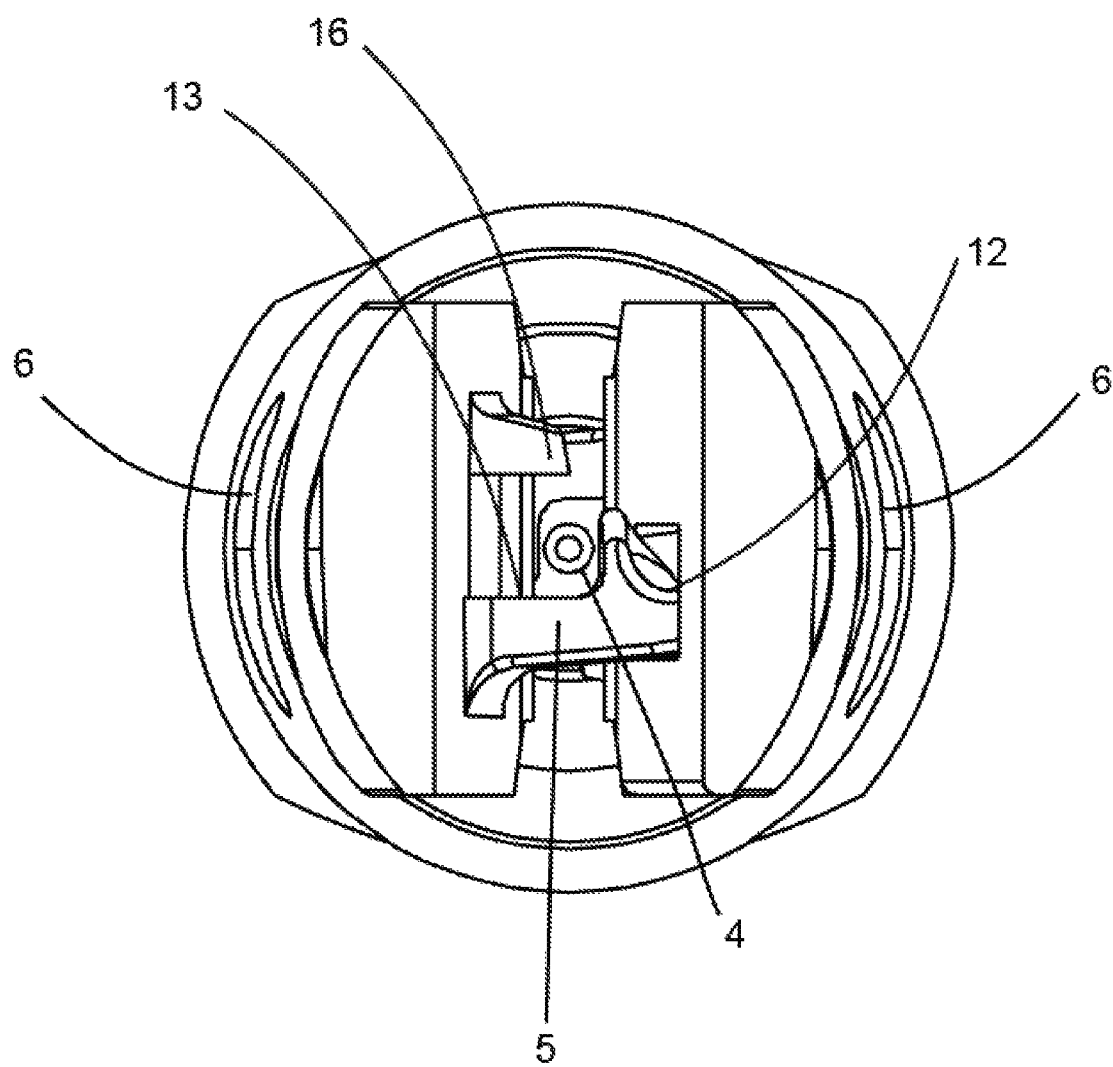
FIG. 11 is a section view of Guard lock features of an embodiment of a Needle Guard assembly, as shown behind the front face.

Referring to FIGS. 10 and 11, there is shown a section view of Guard 1 on Needle 2, in a third position of the assembly after use and pressure is applied on indentation 6 to close Guard 1 around Needle Shaft 4 again. This view shows the Shaft locks 5 positioning onto the Needle Shaft 4. These locks position from the position shown in FIG. 9 to the position shown in FIGS. 10 and 11, where Needle Shaft 4 moves past grooves 14 and into permanent lock groove 13 of locks 5. In an embodiment, grooves 13 are configured so that once Shaft 4 is pushed into grooves 13, Guard 1 will not open again merely by pressing against face 7 of the Guard (in contrast to when Shaft was in the grooves 12 of the initial position shown in FIG. 8.

FIG. 11 shows the two positions of the Needle Shaft lock 5 in an embodiment. Position 1 (shown as 12) can be used during the storage, transport or use of the Needle and can be engaged and disengaged relatively easily. Position 2 (shown as 12) is a more permanent lock on the Needle Shaft 4. This more permanent position is achieved by means of pressing on the finger indentations 6 towards the Needle Shaft 4, to lock the Guard on the Needle to resist further use of the Needle as the more permanent position of the lock 5 resist further exposure of Needle Tip 12 past Guard face 7.

Figure 12:
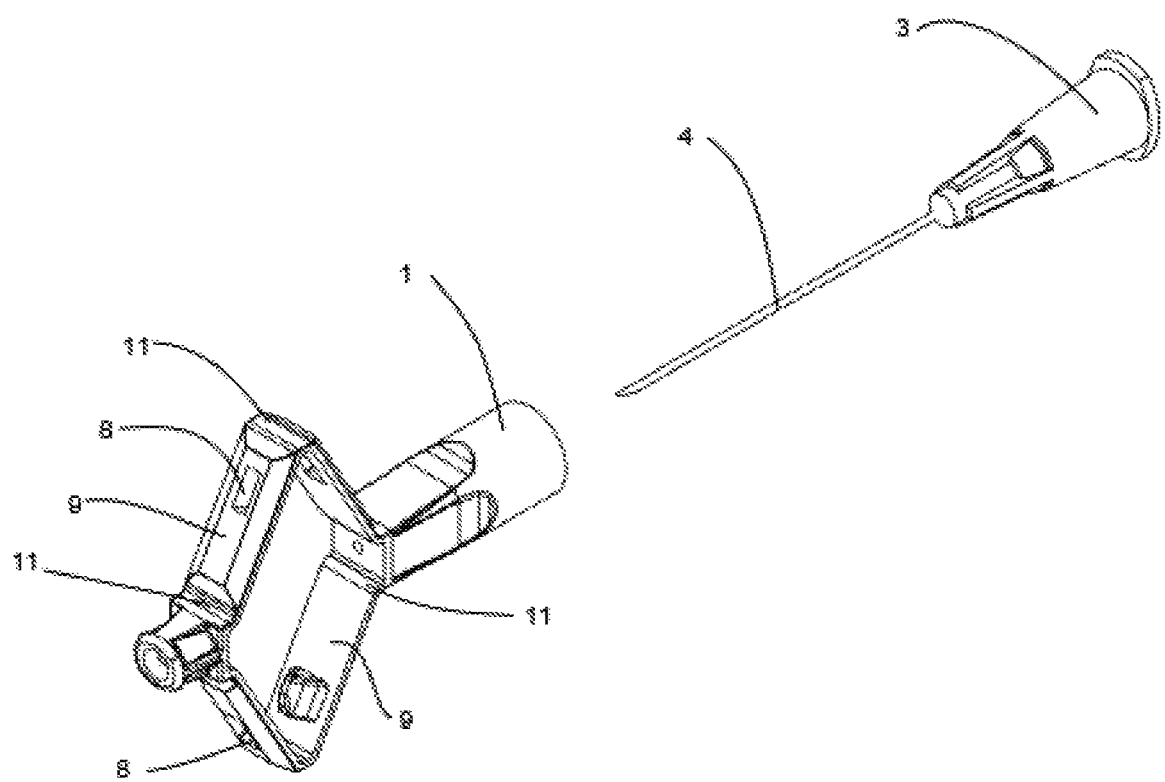
FIG. 12 is an isometric view showing a Needle and a Needle Guard assembly in exploded view.

FIG. 12 shows a Needle Guard 1 and Needle 2 in an exploded view before they are assembled, such as by permanently bonding.

Figure 13:
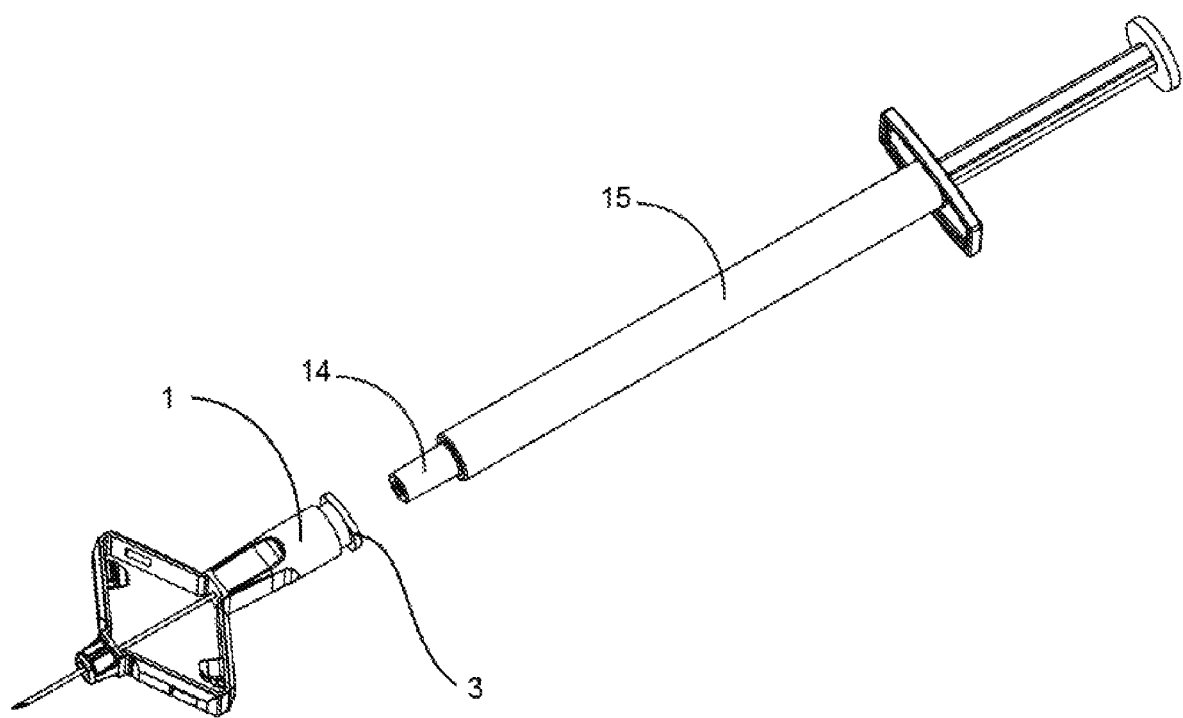
FIG. 13 is an isometric view showing a Needle Guard assembly in relation to an hypodermic syringe body.

FIG. 13 shows a Needle Guard 1 and Needle 2 assembly, about to be installed on a hypodermic Needle body 15.

Figure 14:
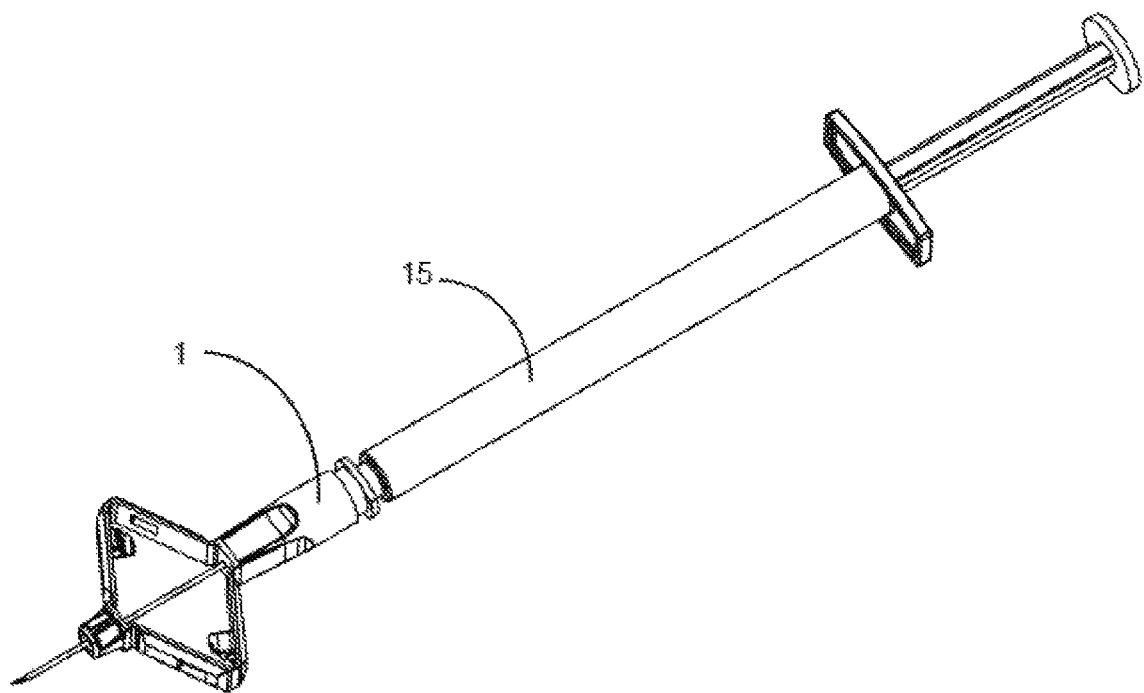
FIG. 14 an isometric view showing a Needle Guard assembly assembled to an hypodermic syringe body.

FIG. 14 shows a Needle Guard 1 and Needle 2 installed on a hypodermic Needle 15.

Figure 15:
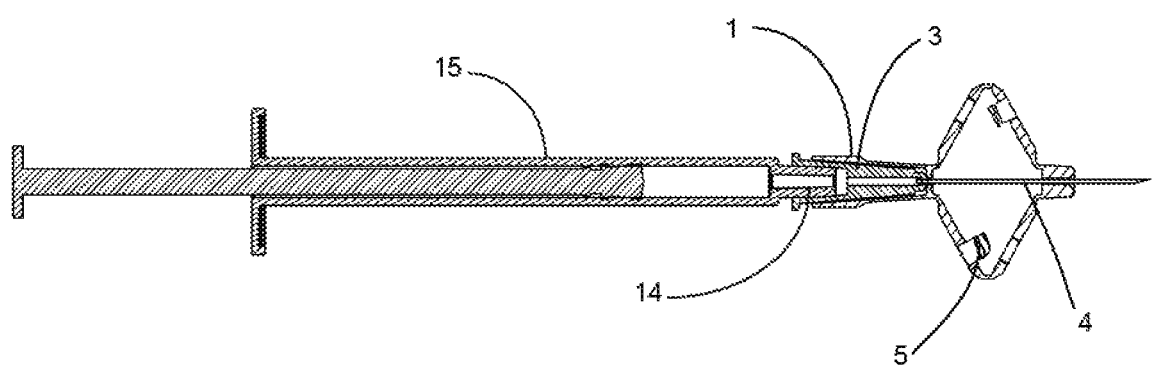
FIG. 15 is a section view of the assembled Needle Guard assembly and hypodermic syringe body of FIG. 14.

FIG. 15 shows a section view of an assembled Needle Guard and Needle, showing that the Needle body 3 is locked into and on a Luer lock 14 of hypodermic Needle body 15.

Figure 16:
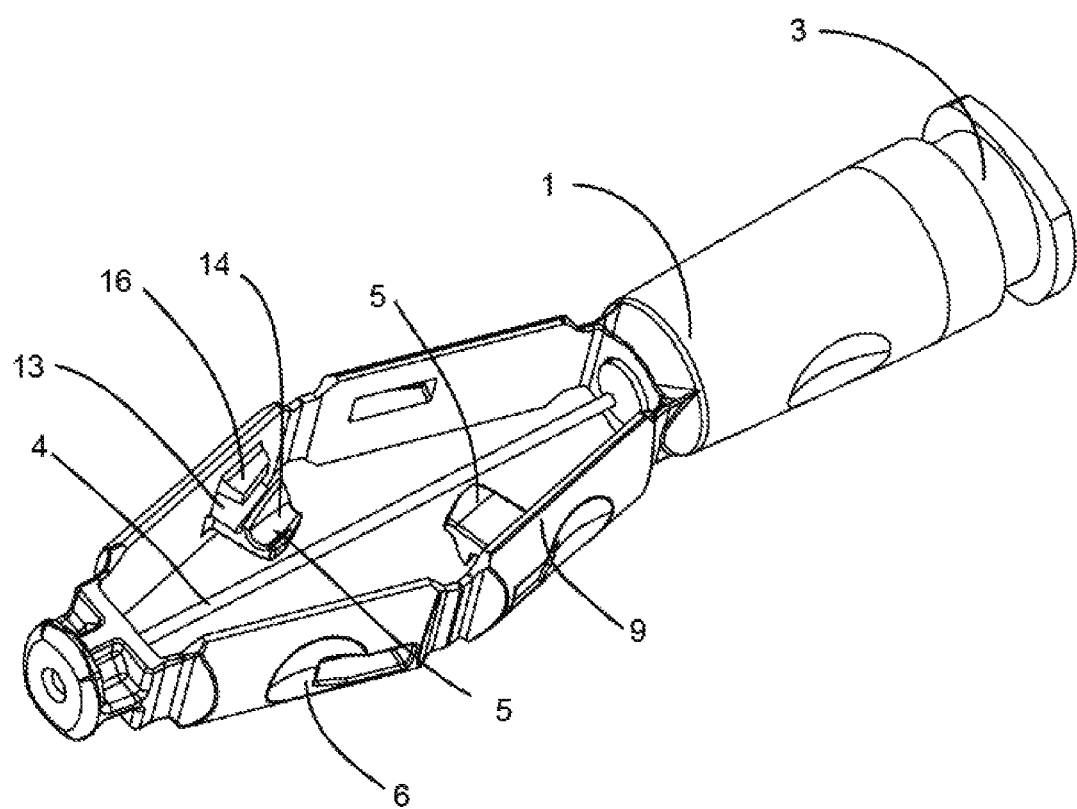
FIG. 16 is an isometric view of the Needle Guard assembly of FIG. 1 in the partially open position.

FIG. 16 shows the Needle and Guard in the partially open position, showing the shapes on the Guard arm with the shaft lock 5 and a secondary lock guard feature 16. As can be seen, the lock guard feature 16 of this embodiment work with groove 13 to lock Needle Shaft 4 once Shaft 4 moves past groove 14, such that Guard 1 will not open again merely by pressing against face 7 of the Guard (once the Needle Shaft 4 is within groove 13 and lock guard feature 16).

Figure 17:
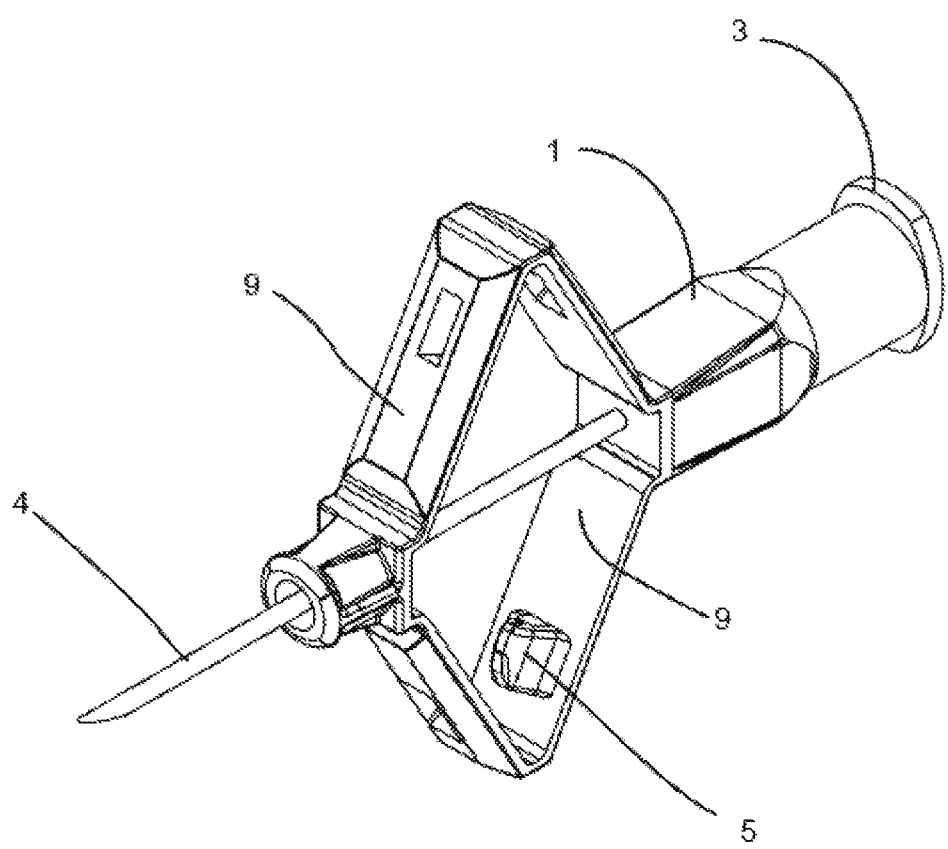
FIG. 17 is an isometric view of the Needle Guard of FIG. 1 in a partially open position.

FIG. 17 shows the Needle Guard in the partially open position, such as while moving from a less open position to a more open position. In an embodiment where it is an integrated product, the Needle may be manufactured with the Guard and thereby configured so as it cannot be removed from the body. In an embodiment, the hub surround Guard incorporates the slip and twist luer lock features of the hypodermic needle hub.

Figure 18:
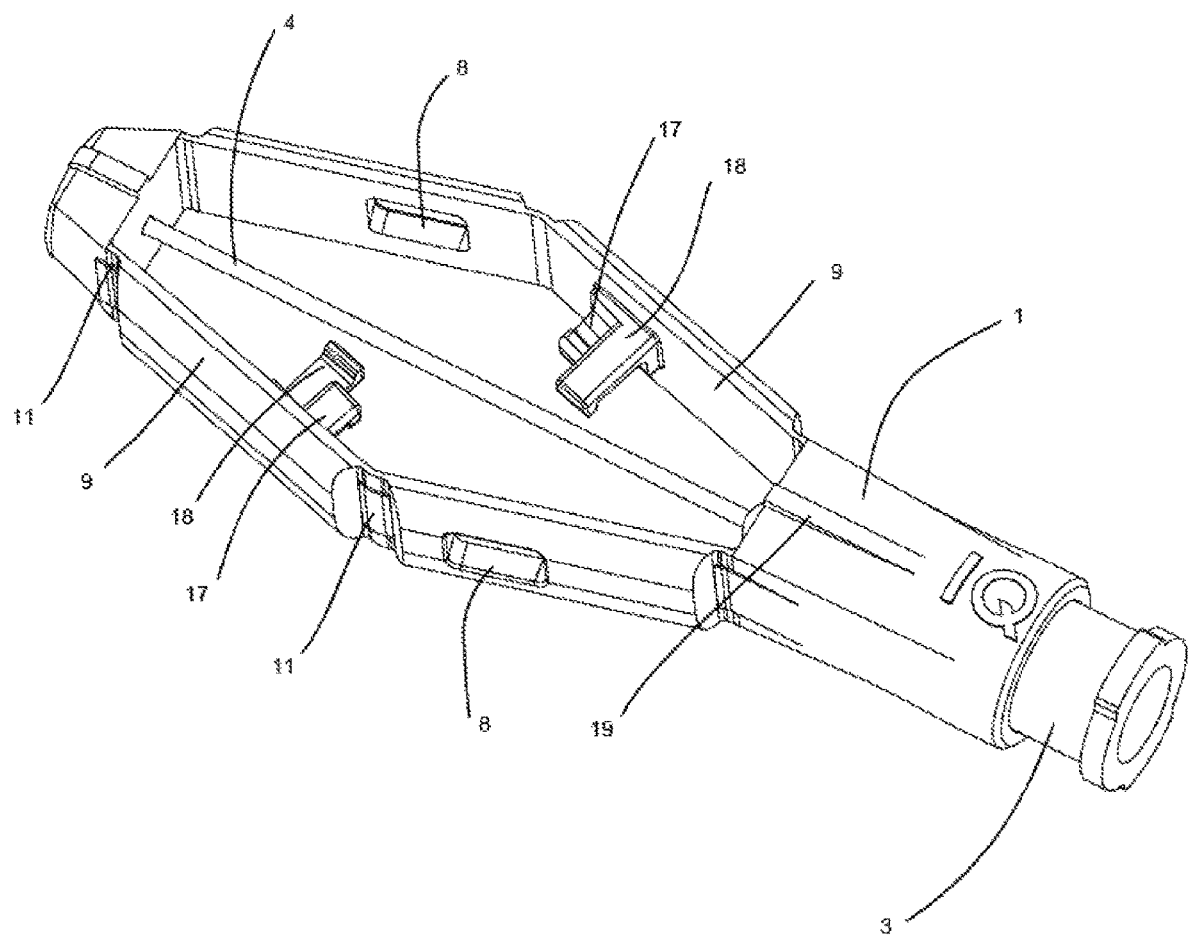
FIG. 18 is an isometric view of an embodiment of a Needle Guard assembly in a first position.

FIG. 18 shows another embodiment of a Needle Guard assembly in a partially open position. In the embodiment, alternate shaft locking, or retention, features are shown for capturing a Needle shaft 4. In the embodiment, the locking or retention features are shown as retention features arms, or capture arms, 17 and 18, with a primary lock capture or retention feature (such as a first groove) on one arm 17 and the secondary lock capture or retention feature (such as a second groove) on the second arm 18. In this embodiment, the splitting of retention features into two independent arms creates multiple forces that capture and lock the Needle 4 into differing use positions. In the embodiment, first and second arms 17 and 18 are configured to provided lock capture features (such as grooves) at different distances from arm 9, to provide multi-stage position holding or locking.

Figure 19:
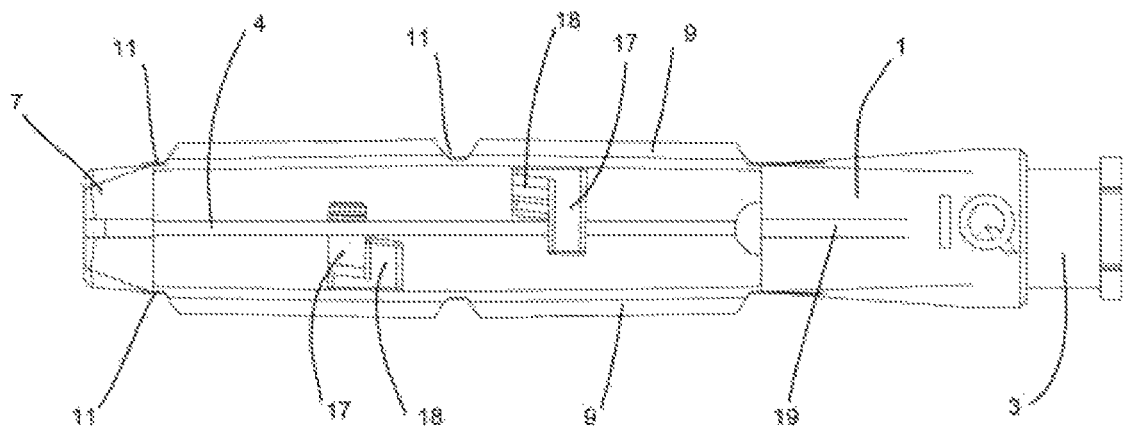
FIG. 19 is a top view of the Needle Guard Needle assembly of FIG. 18 in a second position.

FIG. 19 shows a top view of the alternate embodiment of a Needle Guard in the closed, or partially locked, position. The view shows the feature retention arms 17 and 18 capture of a Needle Shaft 4 by into a first position where Shaft 4 is within the retention feature (such as a groove) of arm 17, but before the locking feature (such as a groove) of arm 18.

Figure 20:
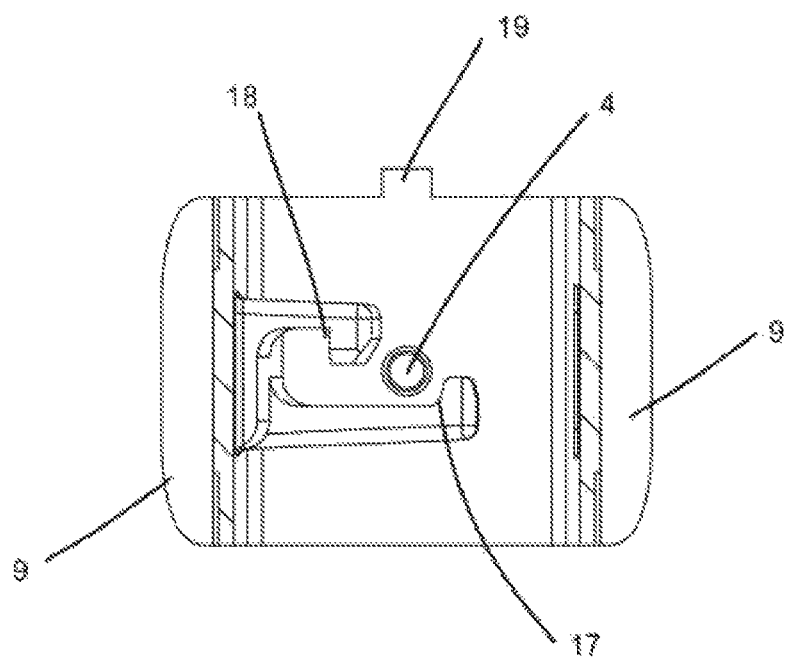
FIG. 20 is a front section view of an embodiment of a Needle Guard assembly having alternate shaft lock features.

FIG. 20 shows a section view of the Needle Guard assembly of FIG. 19 in a partially locked position. In this view the Needle Shaft 4 is shown in a first position held by the retention feature of an arm 17. As shown, the secondary lock position has not been engaged, but can be upon arms 9 being compressed to engage the retention feature of arm 18.

Figure 21:
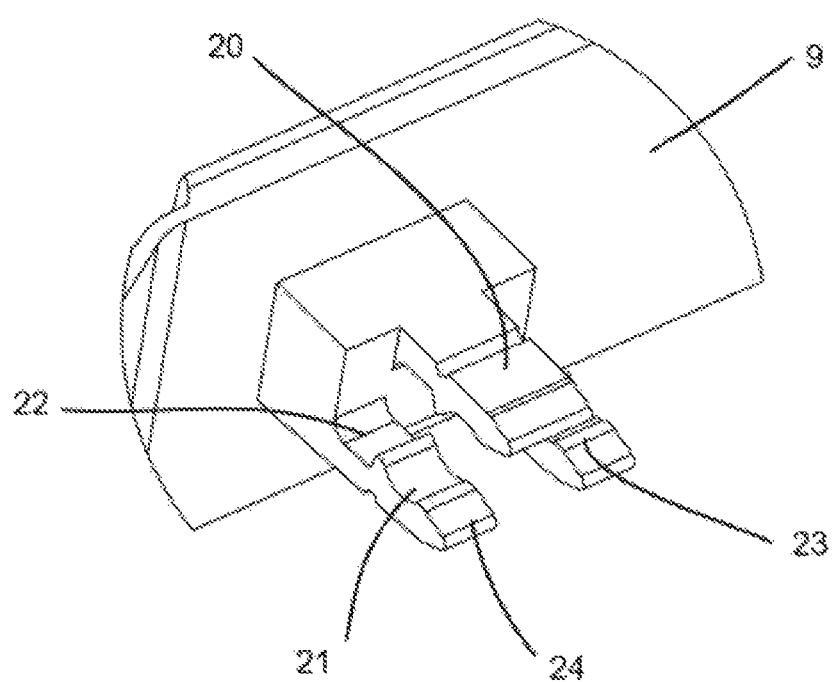
FIG. 21 is an isometric view of an embodiment of shaft lock features in a Needle Guard assembly.

It will be appreciated that additional arms and/or locking feature may be used. For example, FIG. 21 shows a detailed isometric view of another embodiment of a Needle Guard's shaft capturing features. In the embodiment shown, three retention features, or capture, arms 20, 23 and 24 are shown, each having thereon grooves 21 and 22. In the embodiment, grooves 21 and 22 provide primary and secondary locks to capture a Needle Shaft 4 into first and secondary locked positions as arms 9 are compressed as described above.

The present invention has been described regarding preferred embodiments. However, it will be obvious to persons skilled in the art that a few variants and modifications can be made without departing from the scope of the invention as described herein.

What is claimed is:

1. A guard apparatus for a hypodermic needle with a needle shaft, the guard apparatus comprising:
   a needle surround having a needle shaft receiving passageway extending between a proximal end and a distal end of the guard apparatus;
   an arm extending from the needle surround and having a first hinge extending from a front face of the distal end and a second hinge positioned extending from a body of the proximal end, the first hinge and second hinge having a thinned section of deformable plastic;
   a first retention feature extending from the arm to removably engage and disengage with the needle shaft in order to deter and permit movement of the arm between a first position and a second position, the first retention feature includes a first engagement block on a first retention feature arm extending a first distance from the arm; and
   a second retention feature maintains the arm in a locked position, the second retention feature includes a second engagement block on a second retention feature arm extending a second distance from the arm, the second distance being shorter than the first distance.

2. The guard apparatus of claim 1, wherein the first and second retention features are each triangular in shape and less than 60% of the diameter of the needle shaft.

3. The guard apparatus of claim 1, wherein the first retention feature includes a first set of grooves.

4. The guard apparatus of claim 3, wherein the second retention feature includes a second set of grooves.

5. The guard apparatus of claim 1, wherein the needle surround is molded together with the arm.

6. The guard apparatus of claim 5, wherein the guard apparatus is integrated with a needle body housing of the hypodermic needle connected to the needle shaft.

7. The guard apparatus of claim 5, wherein the guard apparatus is attachable to a needle body housing of the hypodermic needle connected to the needle shaft.

8. The guard apparatus of claim 7, wherein the guard apparatus includes a luer lock attachable to the needle body housing.

* * * * *